US012810420B2

(12) United States Patent
Tai

(10) Patent No.: US 12,810,420 B2
(45) Date of Patent: Nov. 24, 2026

(54) METHOD AND SYSTEM FOR ASSESSING NASH CIRRHOSIS

(71) Applicant: HISTOINDEX PTE LTD, Singapore (SG)

(72) Inventor: Chi Shang Tai, Singapore (SG)

(73) Assignee: HISTOINDEX PTE LTD, Singapore (SG)

( * ) Notice: Subject to any disclaimer, the term of this patent is extended or adjusted under 35 U.S.C. 154(b) by 295 days.

(21) Appl. No.: 18/700,525

(22) PCT Filed: Nov. 11, 2022

(86) PCT No.: PCT/SG2022/050825
§ 371 (c)(1),
(2) Date: Apr. 11, 2024

(87) PCT Pub. No.: WO2023/086032
PCT Pub. Date: May 19, 2023

(65) Prior Publication Data

US 2025/0265705 A1 Aug. 21, 2025

Related U.S. Application Data

(60) Provisional application No. 63/263,905, filed on Nov. 11, 2021.

(30) Foreign Application Priority Data

Nov. 4, 2022 (SG) ........................... 10202251635V

(51) Int. Cl.
*G06T 7/00* (2017.01)
*G16H 30/40* (2018.01)
*G16H 50/20* (2018.01)

(52) U.S. Cl.
CPC ........... *G06T 7/0012* (2013.01); *G16H 30/40* (2018.01); *G16H 50/20* (2018.01);
(Continued)

(58) Field of Classification Search
CPC ......... G06T 7/0012; G06T 2207/10056; G06T 2207/10064; G06T 2207/30024;
(Continued)

(56) References Cited

U.S. PATENT DOCUMENTS

2013/0060139 A1* 3/2013 Richter ................ A61B 5/6876 600/438
2015/0148658 A1* 5/2015 Smith .................... A61B 5/055 600/443

(Continued)

FOREIGN PATENT DOCUMENTS

WO WO 2019/077108 A2 4/2019
WO WO 2022/191781 A1 9/2022

OTHER PUBLICATIONS

International Search Report dated Jul. 26, 2023 for corresponding PCT Application No. PCT/SG2022/050825 (4 pages).

(Continued)

*Primary Examiner* — Oneal R Mistry
*Assistant Examiner* — Jongbong Nah
(74) *Attorney, Agent, or Firm* — Womble Bond Dickinson (US) LLP

(57) ABSTRACT

A method for assessing nonalcoholic steatohepatitis (NASH) cirrhosis in a liver biopsy sample includes extracting, from the liver biopsy sample, image data indicative of one or more histopathological features, wherein the one or more histopathological features comprise septa and/or nodules and/or fibrosis, and analysing the extracted image data, using a machine learning model trained to assess the one or more histopathological features, to determine a degree of (Continued)

NASH cirrhosis. Training the machine learning model includes providing a plurality of training samples and a plurality of validation samples, each sample comprising a graded liver biopsy sample; quantifying parameters of the one or more histopathological features from image data of each of the training samples; selecting a subset of quantified parameters of the one or more histopathological features; constructing a model for assessing the one or more histopathological features from the subset of quantified parameters; and validating the constructed model using the validation samples.

17 Claims, 11 Drawing Sheets

(52) U.S. Cl.
CPC ............... *G06T 2207/10056* (2013.01); *G06T 2207/10064* (2013.01); *G06T 2207/30024* (2013.01); *G06T 2207/30056* (2013.01)

(58) Field of Classification Search
CPC ........... G06T 2207/30056; G06T 2207/20084; G16H 30/40; G16H 50/20
See application file for complete search history.

(56) References Cited

U.S. PATENT DOCUMENTS

| | | | | | |
|---|---|---|---|---|---|
| 2015/0339816 | A1* | 11/2015 | Yu | G06T 7/10 | 382/128 |
| 2016/0042514 | A1* | 2/2016 | Amat Roldan | A61B 8/0891 | 382/131 |
| 2018/0024064 | A1* | 1/2018 | Ho | G01N 21/636 | 250/459.1 |
| 2018/0075600 | A1* | 3/2018 | Cales | G06T 7/90 | |
| 2021/0192722 | A1* | 6/2021 | Brozek | G06N 3/04 | |

OTHER PUBLICATIONS

Written Opinion dated Jul. 26, 2023 for corresponding PCT Application No. PCT/SG2022/050825 (8 pages).
Noureddin M et al. Development of Machine Learning Histological Scores that Correlated with Portal Pressures and Development of Varices in NASH patients with Cirrhosis. Nov. 15, 2021 [Retrieved on Jul. 1, 2023 from https://www.histoindex.com/wpcontent/u pl oads/2023/01 /Deve lo pme nt-of-Ma chine-Learn i ng-H isto log ica lScores-that-Correlated-with-Portal-Pressures-and-Development-of-Varices-in-NASH-patients-with-Cirrhosis-v1 .0.pdf].
Bosch J. et al., A Machine Learning Approach to Liver Histological Evaluation Predicts Clinically Significant Portal Hypertension in NASH Cirrhosis. Hepato/ogy, Aug. 1, 2021, vol. 74, No. 6, pp. 3146-3160 [Retrieved on Jul. 1, 2023 from https://aasldpubs.onlinelibrary.wiley.com/doi/abs/10.1002/hep.32087] <DOI: 10.1002/HEP.32087].
Taylor-Weiner A. et al., A Machine Learning Approach Enables Quantitative Measurement of Liver Histology and Disease Monitoring in NASH. Hepato/ogy, Jul. 2021, vol. 74, No. 1, pp. 133-147 [Retrieved on Jul. 1, 2023] <DOI: 10.1002/HEP.31750>.
Noureddin M. et al., Use of second-harmonic generation microscopy for automated detection of septa and nodules in needle liver biopsies of NASH cirrhosis. Journal of Hepatology, Jun. 26, 2022, vol. 77, No. S1, pp. S619-S620: FRI509 [Retrieved on Jul. 1, 2023] <DOI: 10.1016/S0168-8278(22)01557-4>.
Nagula S. et al., Histological-hemodynamic correlation in cirrhosis—a histological classification of the severity of cirrhosis. Journal of Hepato/ogy, Sep. 23, 2005, vol. 44, No. 1, pp. 111-117 [Retrieved on Jul. 1, 2023] <DOI: 10.1016/J.JHEP.2005.07.036>.
Tai D. et al., Unique fibrosis progression and regression features in NAFLD, validation of concept in animal and human studies using artificial intelligence analyses (DP-AI). Nov. 15, 2021 [Retrieved on Jul. 1, 2023 from https://www.histoindex.com/wp-content/uploads/2023/01/Unique-fibrosis-progression-and-regression-features-in-NAFLD-V1.0.pdf].
Wang B. et al., Advanced septa size quantitation determines the evaluation of histological fibrosis outcome in chronic hepatitis B patients. Modern Pathology, May 21, 2018, vol. 31, No. 10, pp. 1567-1577 [Retrieved on Jul. 1, 2023] <DOI: 10.1038/s41379-018-0059-x>.

* cited by examiner

METHOD AND SYSTEM FOR ASSESSING NASH CIRRHOSIS

CROSS-REFERENCE TO RELATED APPLICATIONS

This application is a U.S. National Phase Patent Application of International Application Number PCT/SG2022/050825, filed on Nov. 11, 2022, which claims priority to and the benefit of U.S. Provisional Patent Application No. 63/263,905, filed Nov. 11, 2021, and Singaporean patent application number 10202251635V, filed on Nov. 4, 2022, the entire content of each of which is incorporated herein by reference.

FIELD OF INVENTION

The present invention relates broadly, but not exclusively, to methods and systems for assessing nonalcoholic steatohepatitis (NASH) cirrhosis in a liver biopsy sample.

BACKGROUND

Nonalcoholic fatty liver disease (NAFLD) can progress to nonalcoholic steatohepatitis (NASH), which has become the leading cause of cirrhosis overall, the leading cause of liver transplantation in women, and the second leading cause of liver transplantation in men. Emerging therapies are being examined to treat NASH patients, including those with cirrhosis. However, treating cirrhotic patients is complex since quantification of fibrosis is challenging and has been inadequately studied in NASH cirrhosis. Nevertheless, evidence from cirrhosis of other causes, such as chronic hepatitis B and C, suggests that measurement of fibrosis regression is a goal within reach and has opened the door for the development of drugs that target fibrosis (e.g., antifibrotics).

Recent efforts have determined NASH etiology as a cause of cirrhosis and have defined the primary efficacy end points in trials of NASH cirrhosis. Defining the end points has proven challenging, however, because of the lack of data on the natural history and of drugs effective in reversing cirrhosis. Historical evidence has led to using hepatic portal pressure gradient (HVPG) in NASH cirrhosis trials as a primary end point, especially in patients with elevated HVPG. This approach was supported by evidence from cirrhosis of other causes that HVPG correlates with clinical liver events, and improvement of HVPG is associated with clinical benefits.

However, use of HVPG is challenging in NASH cirrhosis trials because this technique is limited to expert academic centers, variabilities in reading in NASH cirrhosis patients, cost and invasiveness of the procedure, and patients' acceptance. Thus, one-stage improvement of fibrosis in NASH cirrhosis patients, especially those with compensated cirrhosis, has been proposed as an alternative to HVPG measurements. Although linear improvement of fibrosis has correlated with improvement in clinical liver events, this assessment has limitations as well: it ignores other important architectural changes in cirrhosis.

The emergence of machine learning (ML) technology in reading liver histology has advanced the field and limited inter- and intra-observer variabilities. A recent study from a NASH cirrhosis clinical trial has found that a ML-based model on trichrome-stained liver biopsy slides can predict clinically significant portal hypertension (CSPH) in NASH cirrhosis patients. However, such ML-based model still has weak correlation and fails to consider certain significant parameters.

A need therefore exists to provide a method and system that can address at least one of the above problems.

SUMMARY

A first aspect of the present disclosure provides a method for assessing nonalcoholic steatohepatitis (NASH) cirrhosis in a liver biopsy sample, the method comprising:

- extracting, from the liver biopsy sample, image data indicative of one or more histopathological features, wherein the one or more histopathological features comprise septa and/or nodules and/or fibrosis; and
- analysing the extracted image data, using a machine learning model trained to assess the one or more histopathological features, to determine a degree of NASH cirrhosis,
- wherein training the machine learning model comprises:
  - providing a plurality of training samples and a plurality of validation samples, each sample comprising a graded liver biopsy sample;
  - quantifying parameters of the one or more histopathological features from image data of each of the training samples;
  - selecting a subset of quantified parameters of the one or more histopathological features;
  - constructing a model for assessing the one or more histopathological features from the subset of quantified parameters; and
  - validating the constructed model using the validation samples.

The image data may be extracted by second harmonic generation (SHG) microscopy and/or two photon excitation fluorescence (TPEF) microscopy.

Selecting the subset of quantified parameters may comprise a sequential feature selection. Validating the constructed model may comprise a leave-one-out validation.

The one or more histopathological features may comprise septa, and quantifying parameters of septa may further comprise determining a ratio of any two of a group consisting of a cellular area within septa, a collagen area within septa and a vessel area within septa.

The one or more histopathological features may comprise a combination of all of septa, nodules and fibrosis. Constructing the model may comprise determining whether the model correlates with hepatic venous pressure gradient (HVPG) measurements. Alternatively, constructing the model may comprise determining whether the model distinguishes a presence of varices. Alternatively, constructing the model may comprise determining whether the model identifies hepatic venous pressure gradient (HVPG) changes outside a predetermined range.

A second aspect of the present disclosure provides a method for evaluating efficacy of a therapeutic intervention, the method comprising

- determining, from a first liver biopsy sample of a subject before the therapeutic intervention, a first degree of NASH cirrhosis using the method as defined in the first aspect;
- determining, from a second liver biopsy sample of the subject after the therapeutic intervention, a second degree of NASH cirrhosis using the method as defined in the first aspect; and
- comparing the first degree and second degree to determine efficacy of the therapeutic intervention.

Another aspect of the present disclosure provides a system for assessing nonalcoholic steatohepatitis (NASH) cirrhosis in a liver biopsy sample, the system comprising:

- a processor; and
- a computer-readable memory coupled to the processor and having instructions stored thereon that are executable by the processor to:
  - receive image data of the liver biopsy sample indicative of one or more histopathological features, wherein the one or more histopathological features comprise septa and/or nodules and/or fibrosis; and
  - analyse the image data, using a machine learning model trained to assess the one or more histopathological features, to determine a degree of NASH cirrhosis,
  - wherein the machine learning model comprises:
    - a quantification module for quantifying parameters of the one or more histopathological features from image data of each of a plurality of training samples, each training sample comprising a graded liver biopsy sample;
    - a selection module for selecting a subset of quantified parameters of the one or more histopathological features;
    - a construction module for constructing a model for assessing the one or more histopathological features from the subset of quantified parameters; and
    - a validation module for validating the constructed model using a plurality of validation samples, each validation sample comprises a graded liver biopsy sample.

The image data may comprise data from a second harmonic generation (SHG) microscope and/or a two photon excitation fluorescence (TPEF) microscope.

The selection module may be configured to select the subset of quantified parameters by a sequential feature selection. The validation module may be configured to validate the constructed model by a leave-one-out validation.

The one or more histopathological features may comprise septa, and the quantification module may be further configured to determine a ratio of any two of a group consisting of a cellular area within septa, a collagen area within septa and a vessel area within septa.

The one or more histopathological features comprises a combination of all of septa, nodules and fibrosis. The construction module may be further configured to determine whether the model correlates with hepatic venous pressure gradient (HVPG) measurements. Alternatively, the construction module is further configured to determine whether the model distinguishes a presence of varices. Alternatively, the construction module is further configured to determine whether the model identifies hepatic venous pressure gradient (HVPG) changes outside a predetermined range.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

The present disclosure describes a machine learning (ML) model that considers key histologic features in nonalcoholic steatohepatitis (NASH) cirrhosis, namely, septa, nodules, and fibrosis, that have not been considered in the traditional histologic assessment. These features correlate with hepatic venous pressure gradient (HVPG) measurements, and combining them with scores that correlate better with HVPG and clinically significant portal hypertension can distinguish the presence of varices and detect meaningful changes in HVPG. The present machine learning histology model can offer a promising new method for NASH cirrhosis trials that may improve the assessment of histologic changes and drug efficacy.

Figure 1:
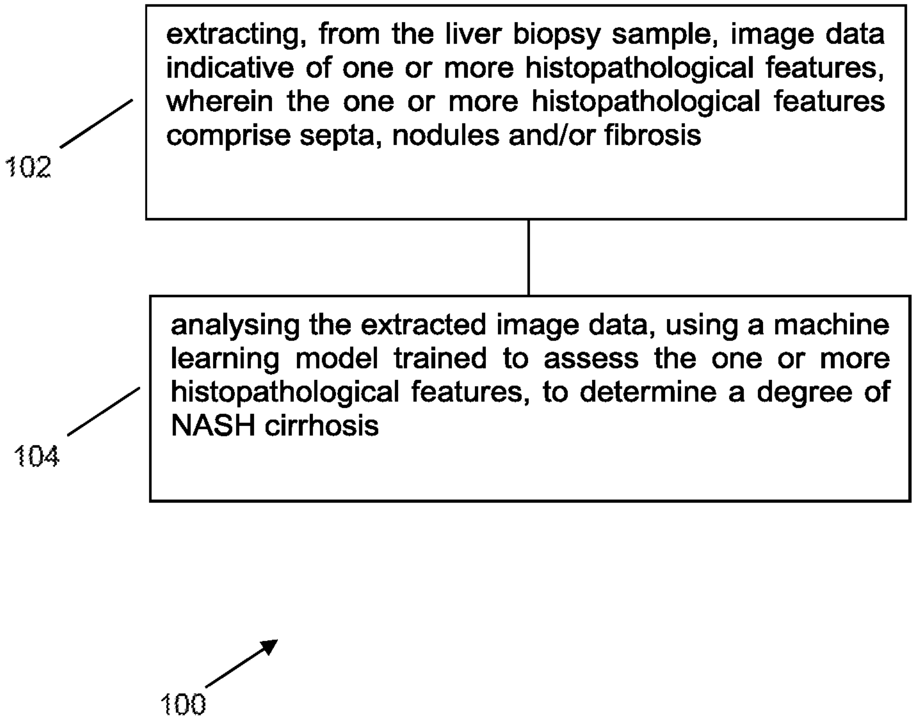
FIG. 1 shows a flow chart illustrating a method for assessing nonalcoholic steatohepatitis (NASH) cirrhosis in a liver biopsy sample according to an example embodiment.

FIG. 1 shows a flow chart 100 illustrating a method for assessing nonalcoholic steatohepatitis (NASH) cirrhosis in a liver biopsy sample according to an example embodiment. At step 101, image data indicative of one or more histopathological features is extracting from the liver biopsy sample. The one or more histopathological features comprise septa and/or nodules and/or fibrosis. For example, some implementations may involve septal features only, other implementations may involve nodular features only, while yet other implementations may involve a combination of any two or all of septa, nodules and fibrosis. At step 104, the extracted image data is analysed, using a machine learning model trained to assess the one or more histopathological features, to determine a degree of NASH cirrhosis.

As discussed in further detail below, training the machine learning model includes providing a plurality of training samples and a plurality of validation samples, each sample comprising a graded liver biopsy sample; quantifying parameters of the one or more histopathological features from image data of each of the training samples; selecting a subset of quantified parameters of the one or more histopathological features; constructing a model for assessing the one or more histopathological features from the subset of quantified parameters; and validating the constructed model using the validation samples.

Embodiments will be described, by way of example only, with reference to the drawings. Like reference numerals and characters in the drawings refer to like elements or equivalents.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as “scanning”, “calculating”, “determining”, “replacing”, “generating”, “initializing”, “outputting”, or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a computer or other device selectively activated or reconfigured by a computer program stored in the computer. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a conventional computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM, GPRS, 3G or 4G mobile telephone systems, as well as other wireless systems such as Bluetooth, ZigBee, Wi-Fi. The computer program when loaded and executed on such a computer effectively results in an apparatus that implements the steps of the preferred method.

The present invention may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC) or Field Programmable Gate Array (FPGA). Numerous other possibilities exist. Those skilled in the art will appreciate that the system can also be implemented as a combination of hardware and software modules.

Example

Study Cohort

Patients with NASH cirrhosis and portal hypertension (HVPG ≥6 mm Hg) were randomized to 52 weeks treatment with drug or placebo. Patients received upper endoscopy within 2 months before randomization and within 14 to 28 days after the final dose of the experimental drug. Varices were classified as small, medium, or large.

HVPG Measurements and Liver Histology

HVPG were performed by advancing a balloon catheter into the hepatic vein under fluoroscopic guidance. Free hepatic pressure was measured when the balloon was completely deflated; wedge pressure was measured upon inflation of the balloon and occlusion of the hepatic vein. Three measurements of the hepatic vein and wedge pressure were obtained and transmitted to an expert HVPG central reader. Liver biopsies of mean length 2.3 cm were obtained. Liver histology was read by an expert liver pathologist central reader. Steatohepatitis was assessed according to Brunt criteria; the NASH activity score, graded according to the NASH clinical research network (CRN), was used to semi-quantify the cellular activity; fibrosis was assessed according to the Ishak score and the NASH clinical research network (CRN) score.

Machine Learning Model

Image Acquisition and Quantification

The images of 240 unstained slides from 120 patients were acquired by use of a second harmonic generation/two-photon excitation fluorescence (SHG/TPE) imaging system (Genesis™ system, HistoIndex Pte. Ltd., Singapore). The collagen and histologic structures were visualized by SHG microscopy and TPE microscopy, respectively. Image tiles were acquired at 20× objective with 512×512 pixels resolution with a dimension of 200×200 μm2. Multiple adjacent tiles were captured to encompass the whole tissue area in each needle biopsy.

The SHG/TPE images of unstained slides were analyzed with a digital image processing algorithm that can quantify 1) 243 septa parameters/criteria, including the morphological characteristics of septa, such as area, length, and width, and the collagen and cellular regions inside the region of septa; 2) 21 nodule parameters/criteria, such as number of nodules and length of nodules; 3) 184 fibrosis parameters/criteria in various regions in liver tissue, including the portal-septa, peri-septal, mid-nodular, peri-venular, and hepatic venule regions. In total, 448 criteria were quantified by the image processing algorithm based on Matlab 2015a (MathWorks, Inc., Natick, MA).

Figure 2:
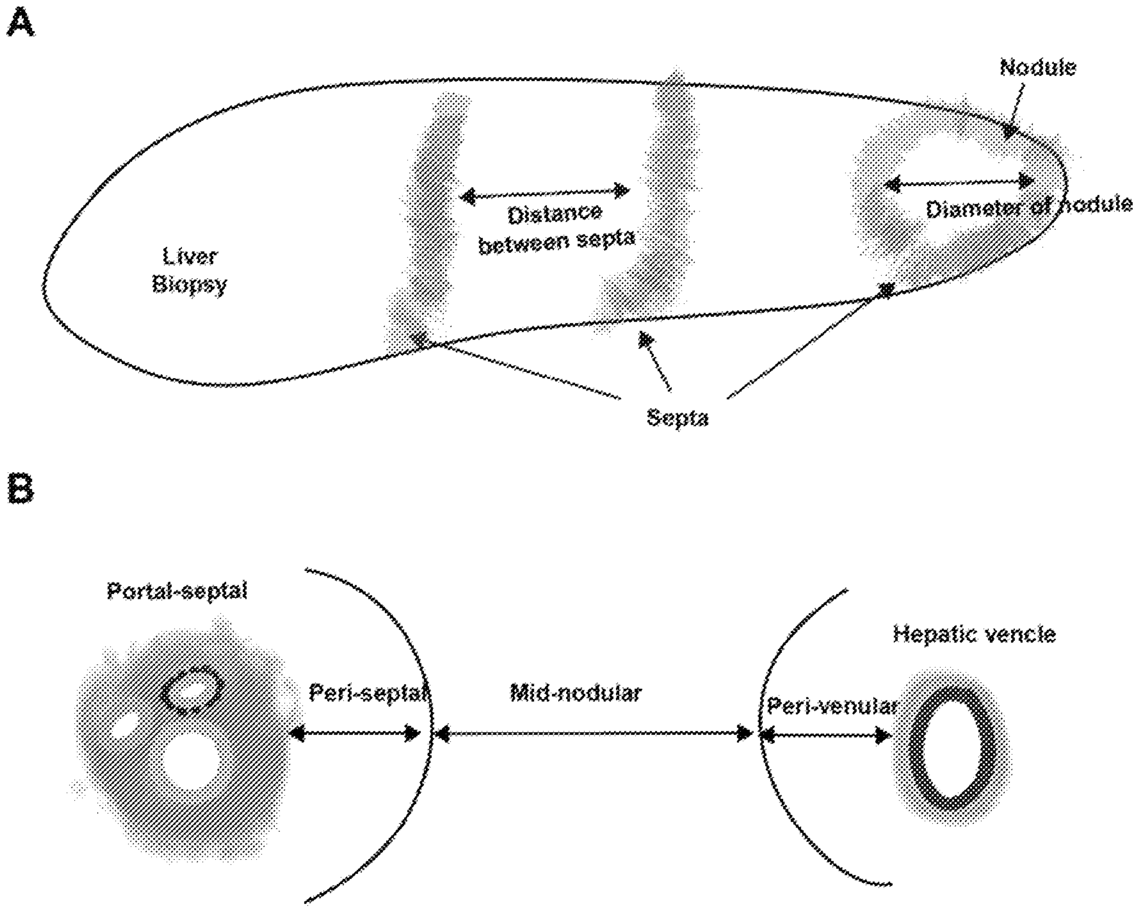
FIG. 2 provides various definitions of regions and measurements according to an example.

Using this machine learning (ML) model, fibrosis was quantified in regions that are specific only to cirrhotic samples. In these cirrhotic samples, the portal tract areas were observed to coincide with septa, and these regions were called “portal-septal”. Centrilobular and peri-portal regions can be difficult to visualize in a cirrhotic liver, but lineage markers such as glutamine synthetase have shown that the peri-septal hepatocyte cells are derived from the centrilobular cells of a normal liver. Given that the peri-portal regions are observed near the septa in these cirrhotic samples, it is designated as "peri-septal". Further, the centrilobular region surrounding central veins in a normal liver does not apply in a cirrhotic nodule, and since the central vein is a tributary of the hepatic vein, peri-central was renamed as "peri-venular", and central vein as "hepatic venule". Lastly, the rest of the parenchyma (Zone 2) of the nodules consists of some regenerative nodules, so they were termed as "mid-nodular" for the purpose of the analysis. The definitions of the regions are illustrated in FIG. 2. Specifically, FIG. 2A provides an illustrative example of a liver biopsy showing septa, nodules, diameter of nodule, and distance between septa as defined by the algorithm. FIG. 2B provides an illustrative example showing the 5 regions in which fibrosis is quantified: portal-septal, peri-septal, mid-nodular, peri-venular, and hepatic venule.

Figure 3:
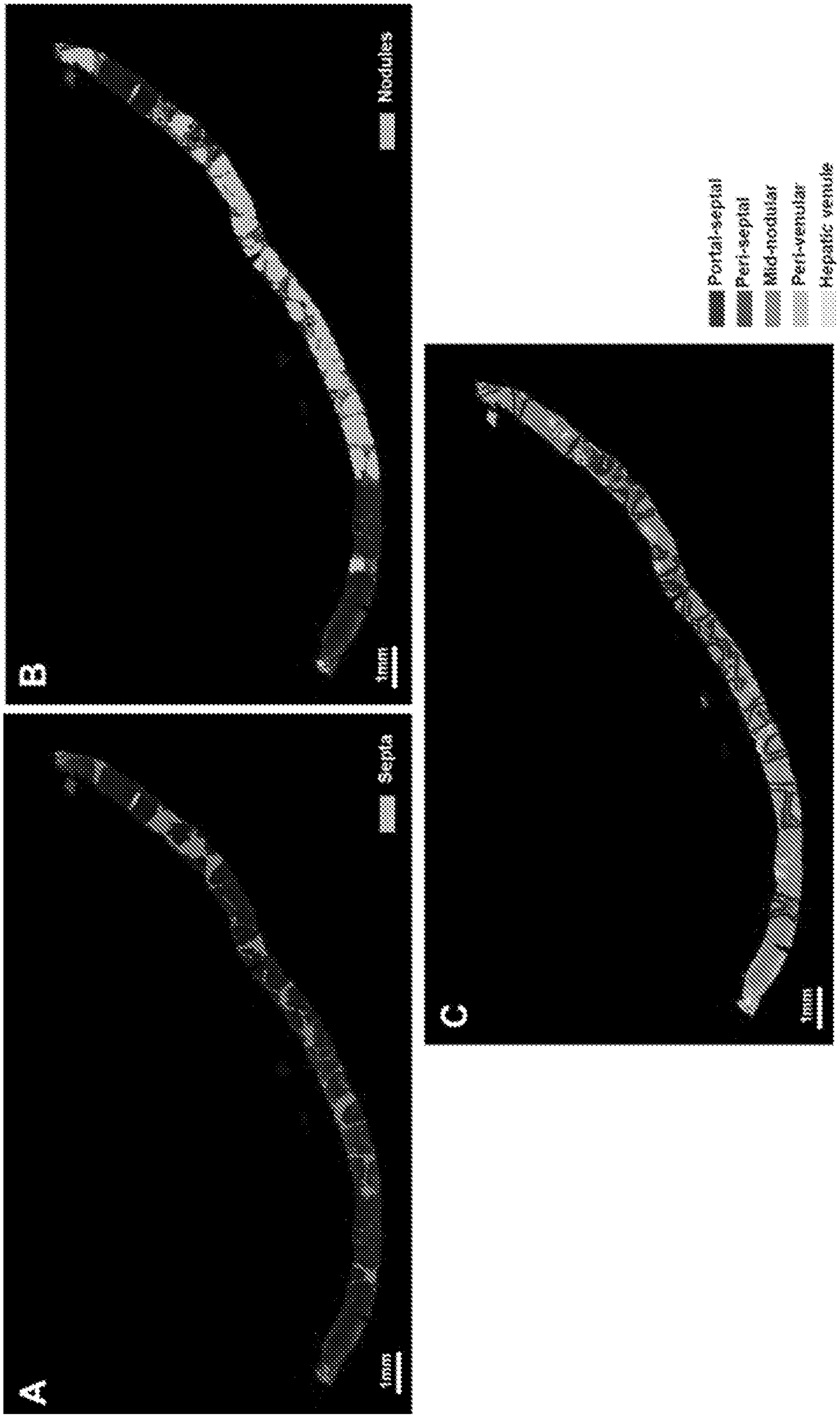
FIG. 3 provides SHG/TPE images showing the AI annotations of septa (A) and nodules (B), with fibrosis (C) analyzed in the portal-septal and peri-septal regions.

Using SHG/TPE, the visualization of these fibrosis in these regions, as well as septa and nodules were shown. FIG. 3 includes SHG/TPE images showing annotations of septa (A) and nodules (B), with fibrosis (C) analyzed in the portal-septal and peri-septal regions by artificial intelligence (AI). In one example, using the ML model, 14 septa and 17 nodules were detected while fibrosis was quantified in the regions as described above.

Model Construction

Figure 4:
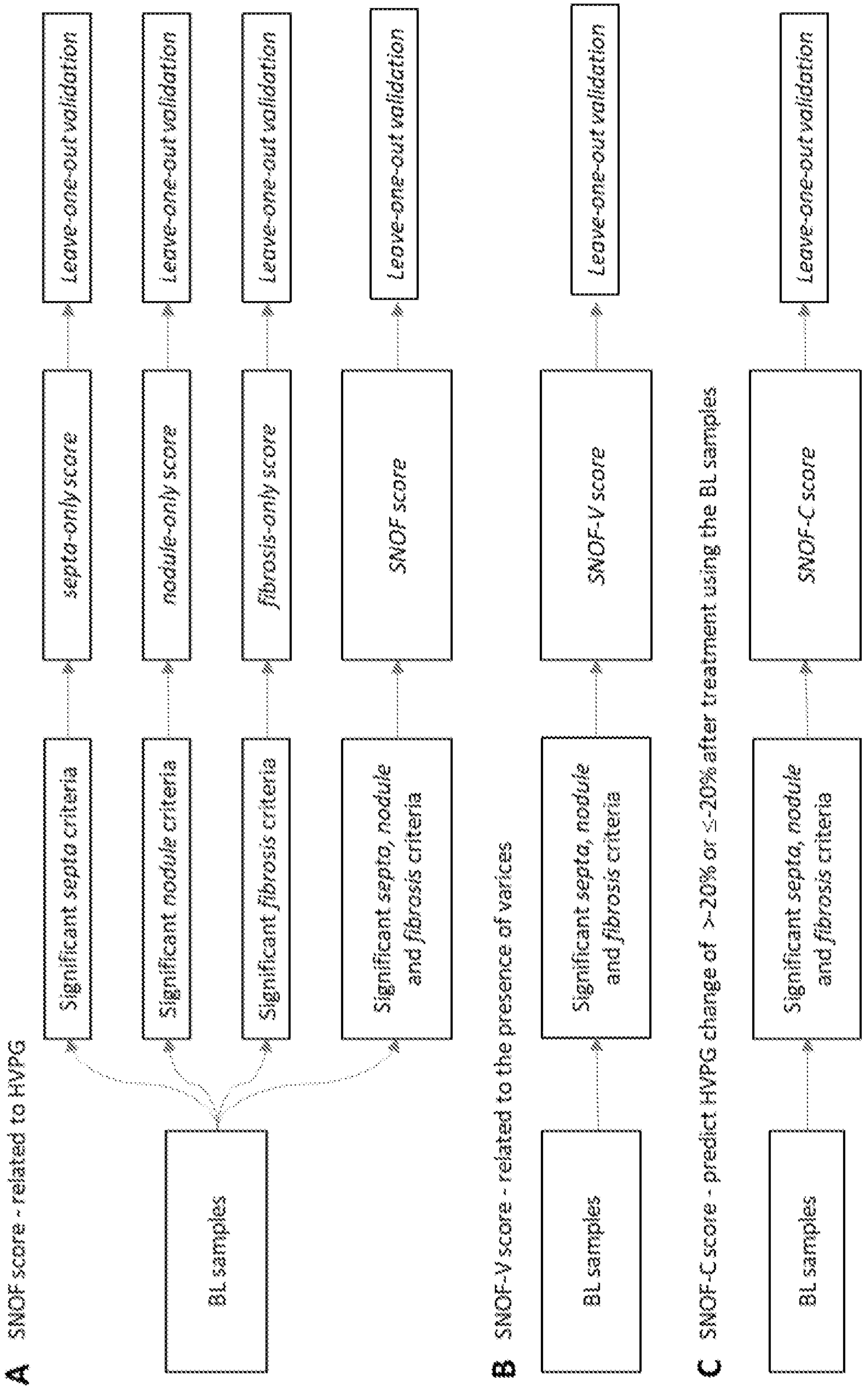
FIG. 4 shows block diagrams illustrating model construction and validation workflows for SNOF, SNOF-C and SNOF-V scores according to an example embodiment.

The model construction and the validation workflows are summarized in FIG. 4. To assess the HVPG for patient, septa, nodules, and fibrosis criteria on baseline samples were used for building single scores, which were named as septa-only score, nodule-only score and fibrosis-only score, respectively. Furthermore, a SNOF score was built by combining septa, nodules, and fibrosis criteria on baseline samples (FIG. 4A). Alternatively or in addition, the above scores can be trained from end-of-treatment samples.

A SNOF-V score was related to the presence of varices. It was built by combining the septa, nodules, and fibrosis criteria on baseline samples (FIG. 4B). Alternatively or in addition, the SNOF-V can be trained from end-of-treatment samples.

A SNOF-C score was to predict HVPG change of >−20% or ≤−20% (i.e. a reduction of 20%, which may be considered meaningful or significant) after treatment using the baseline samples. It was trained using the septa, nodules, and fibrosis criteria from the baseline samples (FIG. 4C).

In other words, the septa, nodules, and fibrosis parameters were combined to build three models designated as 1) a SNOF score that is related to HVPG, 2) a SNOF-V score that is related to the presence or development of varices, and 3) a SNOF-C score that is related to HVPG change of >−20% or ≤−20% between baseline and end-of-treatment regardless of the treatment arm.

Baseline liver biopsies were used as the training set for the models. With a sequential feature selection method, three sets of 15 parameters each were selected from the 448 parameters for SNOF score, SNOF-V score and SNOF-C score, respectively. Tables 1-3 show lists of 15 septa, nodule and fibrosis parameters for SNOF score, SNOF-V score and SNOF-C score, respectively. The models were validated with the leave-one-out cross-validation method. The validation may also involve using variable cohorts to strengthen the findings of training cohorts including combining baseline with end-of-treatment cohorts and leave one-out-cohort.

TABLE 1

List of 15 Septa, Nodule and Fibrosis parameters for SNOF score

| No. | SNOF score criteria | Description |
|---|---|---|
| 1 | % Long Septa | Proportion of septa with length >500 μm |
| 2 | NoLongFiberDis | Number of long and distributed fiber in septa per one septum |
| 3 | NoThickFiberDis | Number of thick and distributed fiber in septa per one septum |
| 4 | NoThickFiberDisH | Number of thick and distributed fiber in septa (for high brightness SHG) per one septum |
| 5 | NoLongFiberDisL | Number of long and distributed fiber in septa (for low brightness SHG) per one septum |
| 6 | AreaCRT | Area of cell region in septa per unit tissue area |
| 7 | AveSeptaDist | Average distance between septa |
| 8 | % Nodules | Percentage of nodules in liver tissue |
| 9 | AveWidthAveRatioNodules | Average ratio of nodules width and average septa width |
| 10 | #Micronodules | Number of micronodules per 1 mm2 of liver tissue |
| 11 | StrOrientation | Orientation of all strings for overall region per unit tissue area |
| 12 | StrWidthPTSAgg | Width of aggregated for portal-septal fibrosis per unit tissue area |
| 13 | #LongStrPTSDis | Number of long and distributed for portal-septal fibrosis per unit tissue area |
| 14 | #IntersectionPTS | Number of intersections of all strings for portal-septal fibrosis per unit tissue area |
| 15 | #IntersectionHV | Number of intersections of all strings for hepatic venule region per unit tissue area |

In one non-limiting example, Spearman's correlation was used to calculate the correlation between the parameters and HVPG values.

TABLE 2

List of 15 Septa, Nodule and Fibrosis parameters for SNOF-V score

| No. | SNOF-V score criteria | Description |
|---|---|---|
| 1 | % Long Septa | Proportion of septa with length >500 μm |
| 2 | NoFiberDis | Number of distributed fiber in septa per one septum |
| 3 | NoShortFiberDis | Number of short and distributed fiber in septa per one septum |
| 4 | FiberPerimeterH | Perimeter of fiber in septa (for high brightness SHG) per one septum |
| 5 | NoLongFiberH | Number of long fiber in septa (for high brightness SHG) per one septum |
| 6 | AggAreaLT | Area of aggregated fiber in septa (for low brightness SHG) per unit tissue area |
| 7 | AveSeptaDist | Average distance between septa |
| | % Nodules | Percentage of nodules in liver tissue |
| 9 | #Micronodules | Number of micronodules per 1 mm2 of liver tissue |
| 10 | AveAreaMicronodules | Average area of micronodules |
| 11 | MaxWidthMaxRatioMicronodules | Maximum ratio of micronodules width and maximum septa width |
| 12 | StrOrientation | Orientation of all strings for overall region per unit tissue area |
| 13 | #IntersectionPTS | Number of intersections of all strings for portal-septal fibrosis per unit tissue area |
| 14 | #ShortStrPeriSepta | Number of short strings for peri-septa region per unit tissue area |
| 15 | #ThinStrPeriPortal | Number of thin strings for peri-portal fibrosis per unit tissue area |

In a non-limiting example, rank sum test was used to assess the difference of the parameters between varices finding YES and NO.

TABLE 3

List of 15 Septa, Nodule and Fibrosis parameters for SNOF-C score

| No. | SNOF-C score criteria | Description |
|---|---|---|
| 1 | % LongSepta | Proportion of septa with length >500 μm |
| 2 | AreaCR/SeptaLength | Total area of cell region in septa/total septa length |
| 3 | #CR/SeptaWidth | Number of cell region/septa width |
| 4 | CollagenAreaLT | Area of collagen in septa (for low brightness SHG) per unit tissue area |
| 5 | AggAreaLT | Area of aggregated fiber in septa (for low brightness SHG) per unit tissue area |
| 6 | AveLengthTissueTile | Average length of tissue tile |
| 7 | AveAreaRatioTile | Average ratio of tissue tile area and septa area |
| 8 | AveWidthMaxRatioTile | Average ratio of tissue tile width and maximum septa width |
| 9 | % Nodules | Percentage of nodules in liver tissue |
| 10 | #Micronodules | Number of micronodules per 1 mm2 of liver tissue |
| 11 | AveAreaRatioNodule | Average ratio of nodule area and septa area |
| 12 | #ThickStrPTS | Number of thick strings for portal-septal fibrosis per unit tissue area |
| 13 | #ThickStrPTSAgg | Number of thick and aggregated for portal-septal fibrosis per unit tissue area |
| 14 | #IntersectionPeriVenular | Number of intersections of collagen string for peri-venular region per unit tissue area |
| 15 | #IntersectionHV | Number of intersections of collagen string for hepatic venule region per unit tissue area |

In a non-limiting example, rank sum test was used to assess the difference of the parameters between HVPG changes ≤−20% and HVPG changes >−20%.

Statistical Analysis

The Spearman non-parametric method was used to estimate the correlation between SNOF score and HVPG. The difference of SNOF-V score between varices YES and NO samples was estimated by the Wilcoxon rank sum test. The area under the receiver operating characteristic curve (AUROC) analysis was performed to evaluate the performance of SNOF and SNOF-V scores. The cut-off values of SNOF score for evaluating the presence significant portal hypertension, the cut-off values of SNOF-V score and the cut-off value for HVPG value for evaluating the presence of esophageal varices, were determined with Youden's index. The sensitivity, specificity, negative predictive value (NPV) and positive predictive value (PPV), determined by the cut-off values, were calculated. Statistical significance level was set at $p<0.05$. Statistical analyses were performed with Matlab 2015a (MathWorks, Inc., Natick, MA).

Detection of Septa, Nodules, and Fibrosis (SNOF)

The machine learning model as described herein can identify septa, nodules, and fibrosis in the biopsy sample and quantifies their morphological features automatically. A total of 243 septa-related, 21 nodule-related, and 184 fibrosis-related morphological features were analyzed for each biopsy sample.

Correlation of the SNOF ML Model with HVPG

The degree of correlation among the septa-, nodules-, and fibrosis-selected criteria was assessed on baseline biopsies, using them as training cohort, and the same biopsies were used as validation cohort by leaving one sample out. The same process (training cohort and the same biopsies as validation cohort by leaving one sample out) was repeated on the end-of-treatment biopsy slides to confirm the results. The results were consistent in the training cohorts and the validation cohorts (Table 4).

TABLE 4

Correlation Results

| Parameters | Correlation results (r value): Training using BL samples | Correlation results (r value): Leave-one-out validation |
|---|---|---|
| Septa only | 0.53 | 0.43 |
| Nodule only | 0.51 | 0.39 |
| Fibrosis only | 0.58 | 0.42 |
| SNOF | 0.67 | 0.53 |

Figure 5:
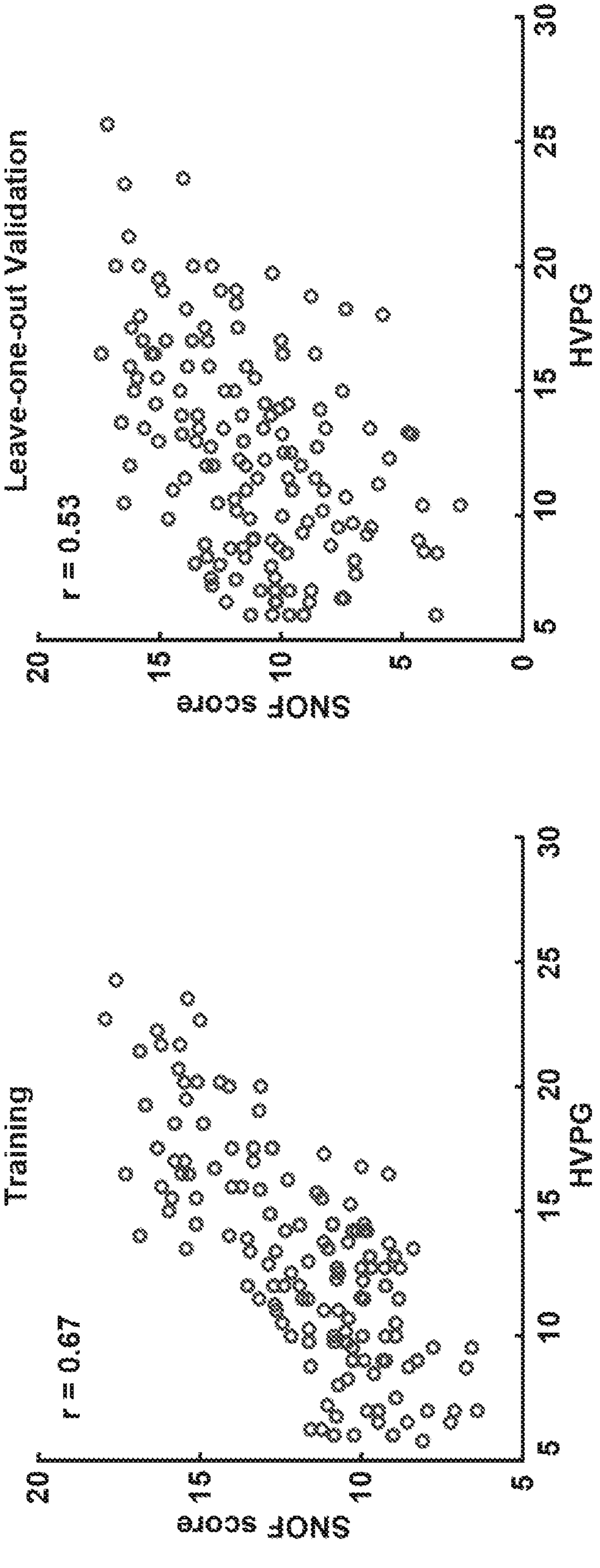
FIG. 5 shows scatter plots for the SNOF score, where training and validation results are provided.

Next, a machine learning SNOF score was built by selecting the 15 best morphological parameters that correlated significantly with HVPG measurement (Tables 1 and 2) from each morphological feature described. The correlation of training and validation results of SNOF scores with HVPG is shown in FIG. 5, with an r value of 0.67 in the training cohort and 0.53 in the validation (leave-one-out) cohort from the baseline biopsy samples. The combination of septa, nodules and fibrosis (SNOF) in an index outperforms using just septa, or nodule, or fibrosis separately, as can be seen from Table 4.

Correlation of the SNOF ML Model with Presence of Varices

Figure 6:
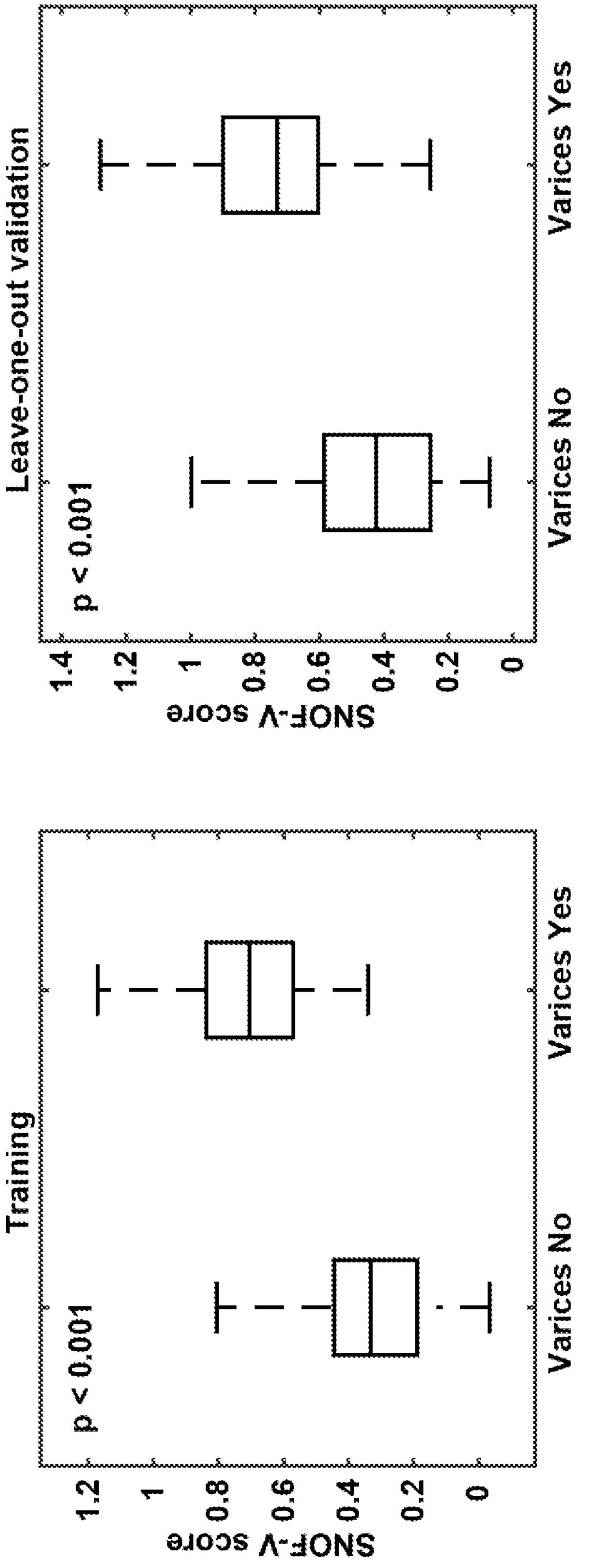
FIG. 6 shows boxplots for the SNOF-V score, where training and validation results are provided.

The SNOF-varices (SNOF-V) scores were created by correlating variables with the presence of varices and selected the 15 best correlated parameters for the final model. The performance of the SNOF-V score to distinguish the presence of esophageal varices at baseline (pre-treatment) training and validation samples is shown in FIG. 6.

Performances of SNOF Score and SNOF-V Scores

An optimum cut-off value of 11.78 was determined by correlating SNOF scores with HVPG value of ≥10 (CSPH). With this cut-off value, the performance SNOF score in predicting HVPG ≥10 is summarized in Table 5 below. Similarly, the performance of SNOF-V score in predicting the presence of varices is also summarized in Table 5. The performance in predicting the presence of varices with a HVPG cut-off value at ≥10 is also included in the table as a reference. We validated the results by combining the baseline and end of treatment samples.

TABLE 5

SNOF and SNOF-V Performance

| | Baseline | | | | | Baseline + End of treatment | | | | |
|---|---|---|---|---|---|---|---|---|---|---|
| | AUC | Sensitivity | Specificity | PPV | NPV | AUC | Sensitivity | Specificity | PPV | NPV |
| SNOF score ≥12.17 distinguished CSPH | 0.85 | 63% | 98% | 98% | 57% | 0.74 | 57% | 83% | 86% | 50% |
| SNOF-V index ≥0.53 distinguished varices | 0.91 | 82% | 88% | 85% | 85% | 0.74 | 62% | 77% | 68% | 72% |
| HVPG ≥10 distinguished varices | 0.74 | 85% | 49% | 59% | 80% | 0.72 | 83% | 48% | 56% | 78% |

Performance of SNOF-C in Detecting Clinically Meaningful HVPG Changes

The patients were divided into those who had HVPG change of >−20% or ≤−20% (i.e. a clinically meaningful reduction) between baseline and end of treatment regardless of the treatment arm. The SNOF-Change (SNOF-C) score was built based on the top 15 significant parameters that correlated with −20% changes in HVPG (Table 3). The SNOF-C score performed well in differentiating those who had >−20% change in HVPG versus those who did not, with AUROC of 0.89 in the training cohort and 0.79 in the validation cohort (see Table 6 below). The performance criteria of SNOF-C score including sensitivity, specificity, PPV, and NPV are shown in Table 6.

TABLE 6

| SNOF-C Performance | | | | | | | | | | |
|---|---|---|---|---|---|---|---|---|---|---|
| | Training | | | | | Leave-one-out validation | | | | |
| | AUC | Sensitivity | Specificity | PPV | NPV | AUC | Sensitivity | Specificity | PPV | NPV |
| SNOF-C score >0.257 to predict HVPG changes ≤−20% | 0.88 | 95% | 72% | 51% | 96% | 0.80 | 76% | 66% | 43% | 87% |

The performance of the machine learning (ML) model as discussed above was also separately evaluated using a set of 25 training samples and a set of 10 validation samples, and the results are summarised in Tables 7 and 8 below. In Tables 7 and 8, "AI" refers to the ML model, "overlap for pathologist" refers to the septa first annotated by an expert pathologist and separately detected by the ML model, while "overlap for AI" refers to the septa first detected by the ML model and separately annotated by the expert pathologist.

TABLE 7

| Performance for the 25 training samples | | | | | | | | |
|---|---|---|---|---|---|---|---|---|
| | Septa | | | | Nodule | | | |
| No. | Pathologist | AI | Overlap for Pathologist | Overlap for AI | Pathologist | AI | Overlap for Pathologist | Overlap for AI |
| 1 | 10 | 13 | 10 | 10 | 11 | 15 | 11 | 12 |
| 2 | 22 | 19 | 21 | 18 | 30 | 29 | 28 | 29 |
| 3 | 8 | 8 | 8 | 8 | 15 | 14 | 12 | 14 |
| 4 | 9 | 12 | 9 | 11 | 28 | 19 | 17 | 19 |
| 5 | 9 | 11 | 8 | 8 | 20 | 21 | 15 | 17 |
| 6 | 12 | 15 | 10 | 9 | 24 | 18 | 21 | 18 |
| 7 | 15 | 17 | 15 | 15 | 25 | 28 | 24 | 26 |
| 8 | 19 | 18 | 19 | 17 | 42 | 44 | 36 | 42 |
| 9 | 11 | 14 | 10 | 10 | 25 | 25 | 22 | 25 |
| 10 | 16 | 11 | 15 | 10 | 33 | 27 | 24 | 26 |
| 11 | 8 | 9 | 7 | 7 | 22 | 18 | 16 | 17 |
| 12 | 17 | 17 | 15 | 16 | 30 | 27 | 26 | 26 |
| 13 | 9 | 7 | 8 | 7 | 19 | 15 | 14 | 15 |
| 14 | 17 | 22 | 16 | 19 | 29 | 26 | 25 | 24 |
| 15 | 30 | 31 | 28 | 28 | 52 | 45 | 48 | 43 |
| 16 | 9 | 8 | 7 | 6 | 15 | 17 | 15 | 17 |
| 17 | 9 | 10 | 9 | 10 | 18 | 16 | 14 | 15 |
| 18 | 15 | 9 | 11 | 10 | 23 | 15 | 17 | 15 |
| 19 | 16 | 15 | 15 | 14 | 31 | 22 | 24 | 22 |
| 20 | 11 | 10 | 10 | 9 | 19 | 17 | 17 | 16 |
| 21 | 16 | 19 | 14 | 18 | 25 | 24 | 22 | 23 |
| 22 | 7 | 14 | 8 | 7 | 25 | 25 | 23 | 24 |
| 23 | 15 | 14 | 14 | 13 | 38 | 34 | 34 | 34 |
| 24 | 11 | 10 | 9 | 10 | 15 | 15 | 11 | 13 |
| 25 | 13 | 11 | 12 | 11 | 23 | 19 | 17 | 17 |
| Total | 334 | 344 | 308<br>Sensitivity<br>92% (308/334) | 301<br>PPV<br>88% (301/344) | 637 | 575 | 533<br>Sensitivity<br>84% (533/637) | 549<br>PPV<br>95% (549/575) |

TABLE 8

| Performance for the 10 validation samples | | | | | | | | |
|---|---|---|---|---|---|---|---|---|
| | Septa | | | | Nodule | | | |
| No. | Pathologist | AI | Overlap for Pathologist | Overlap for AI | Pathologist | AI | Overlap for Pathologist | Overlap for AI |
| 1 | 12 | 11 | 12 | 9 | 30 | 28 | 27 | 27 |
| 2 | 8 | 7 | 8 | 6 | 29 | 23 | 24 | 23 |
| 3 | 24 | 18 | 20 | 20 | 30 | 30 | 28 | 29 |
| 4 | 9 | 7 | 9 | 7 | 42 | 37 | 36 | 35 |
| 5 | 3 | 3 | 3 | 3 | 16 | 15 | 15 | 14 |
| 6 | 12 | 12 | 11 | 10 | 24 | 25 | 23 | 25 |
| 7 | 11 | 12 | 10 | 11 | 28 | 24 | 25 | 24 |
| 8 | 18 | 16 | 16 | 15 | 24 | 26 | 23 | 22 |

TABLE 8-continued

Performance for the 10 validation samples

| | Septa | | | | Nodule | | | |
|---|---|---|---|---|---|---|---|---|
| No. | Pathologist | AI | Overlap for Pathologist | Overlap for AI | Pathologist | AI | Overlap for Pathologist | Overlap for AI |
| 9 | 9 | 9 | 9 | 9 | 32 | 34 | 31 | 32 |
| 10 | 12 | 11 | 11 | 11 | 31 | 29 | 28 | 28 |
| Total | 118 | 106 | 109 Sensitivity 92% (109/118) | 101 PPV 95% (101/106) | 286 | 271 | 260 Sensitivity 91% (260/286) | 259 PPV 96% (259/271) |

By using the ML model as disclosed to analyse image data of baseline and end-of treatment liver biopsy samples taken from the same patient, together with the understanding of NASH, it is possible to evaluate the efficacy of the treatment.

Figure 7:
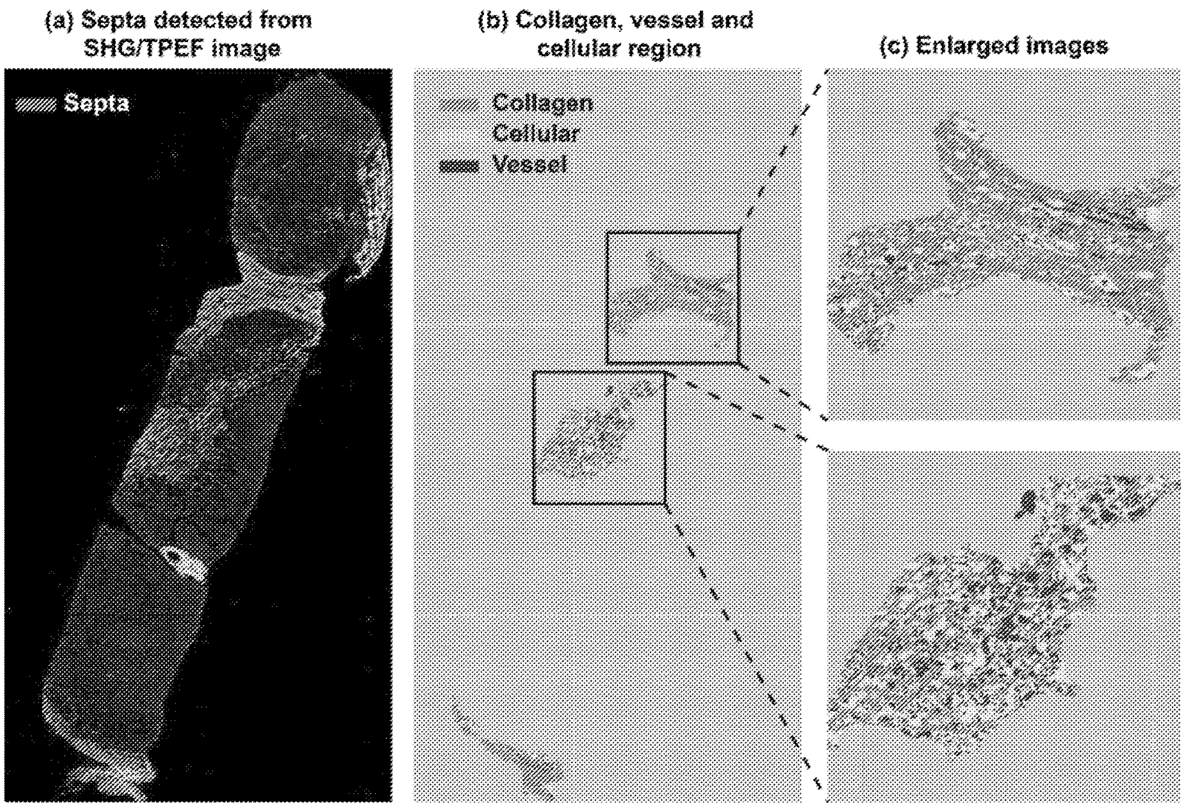
FIG. 7 shows an example of septa detection and the sub-regions within septa.

For example, it is recognised that the features of septa are important to access the severity or liver fibrosis. In one implementation where the ML model is based on septa parameters, an additional parameter indicative of fibrosis progression or regression may be determined based on relative areas of sub-regions within the septa. Generally, septa region can be divided into three sub-regions, including collagen region, cellular region, and vessel region. An example of septa detection and the sub-regions within septa is provided in FIG. 7. The cellular region includes inflammatory cells and hepatocytes. Collagen region refers to the collagen fiber only, and may be referred to as acellular region. The additional parameter may be a cellularity parameter, which is a combined parameter by cellular region and acellular region, called cellular/acellular.

Further, four types of septa have been observed with the progress of septa, including progressive septa, established septa, regressive septa and broken septa. The dynamics of fibrosis progression and regression during re-modeling of the septa is as described below with reference to FIG. 8.

Figure 8:
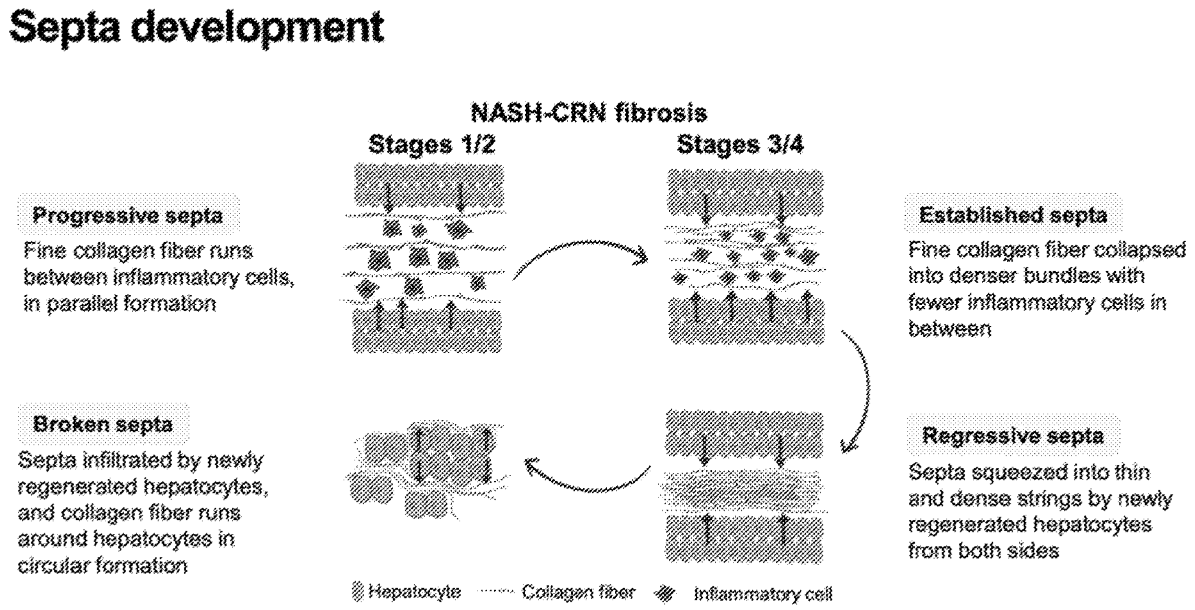
FIG. 8 shows various types of septa and their respective features.

Progression of septa—During the formation of septa, which is typically seen in fibrosis stages 1 or 2 (based on NASH-CRN staging system), one can see clear inflammation, and fine strings of collagen fibres running in between these inflammatory cells. The collagen fibres at this stage appeared in parallel formation as shown in FIG. 8. Meanwhile, one can see hepatocyte regeneration happening outside the septa too, just that the worsening of inflammation and fibrosis dominates the hepatocyte regeneration during this phase.

Establishing of complete septa—As fibrosis progress, one can observe collapse of cellular space (mostly disappearing of inflammatory cells) within progressive septa area, together with hepatocyte regeneration outside the septa pushing into the septa, which results in a denser formation of collagen fibres, which is what typically referred to as a "septa". This "established septa" is the basic definition of Stage 3 fibrosis (based on NASH-CRN staging system), and is also observed in Stage 4 fibrosis.

Regression of septa—In the case where there is effective intervention or regeneration dominates progression of disease, one can start seeing strong hepatocyte regeneration pushing into septa area. This may appear as very thin septa. However, this is still considered as "established septa", and is typically recorded as Stage 3 or Stage 4 fibrosis (based on NASH-CRN staging system).

Breaking of septa—With continual hepatocyte regeneration, one can see hepatocyte infiltration into the septa and eventually breaking the septa into pieces. During this phase of fibrosis, it looks similar to progressive septa (Stages 1/2 based on NASH-CRN staging system) with fine collagen fibres. However, this collagen fibres appear more rounded as they run in between hepatocyte cells, which are typically larger than inflammatory cells.

The example embodiments consider the dynamics and the direction of fibrosis progression/regression when staging fibrosis in clinical trials, which is not currently considered as what is typically done in routine clinical diagnosis.

As discussed above, the amounts of collagen and cells within septa are different between stages. The ratio of cellular region to acellular region can combine these two parameters. This allows for the measurement of the dynamic change of septa. In particular, the change of cellular/acellular is found in example embodiments to be a significant marker for fibrosis progression and regression.

For example, assuming the area of a septum is 1, if the areas of collagen region, cellular region and vessel region are 0.4, 0.5, and 0.1, respectively, the cellular/acellular ratio is 1.25 (=0.5/0.4). If the areas of collagen region, cellular region and vessel region are 0.4, 0.4, and 0.2, respectively, the cellular/acellular ratio is 1 (=0.4/0.4). Progressive septa have clear inflammatory cells, and regressive septa have hepatocyte regeneration in the septa area. The cellular/acellular value for these two kinds of septa may be higher than the established septa and broken septa. It is a key feature for the dynamics of septa.

Similarly, in alternate embodiments, the combination of parameters such as cellular/vessel and collagen/vessel may also provide important information on fibrosis progression and regression.

Figure 9:
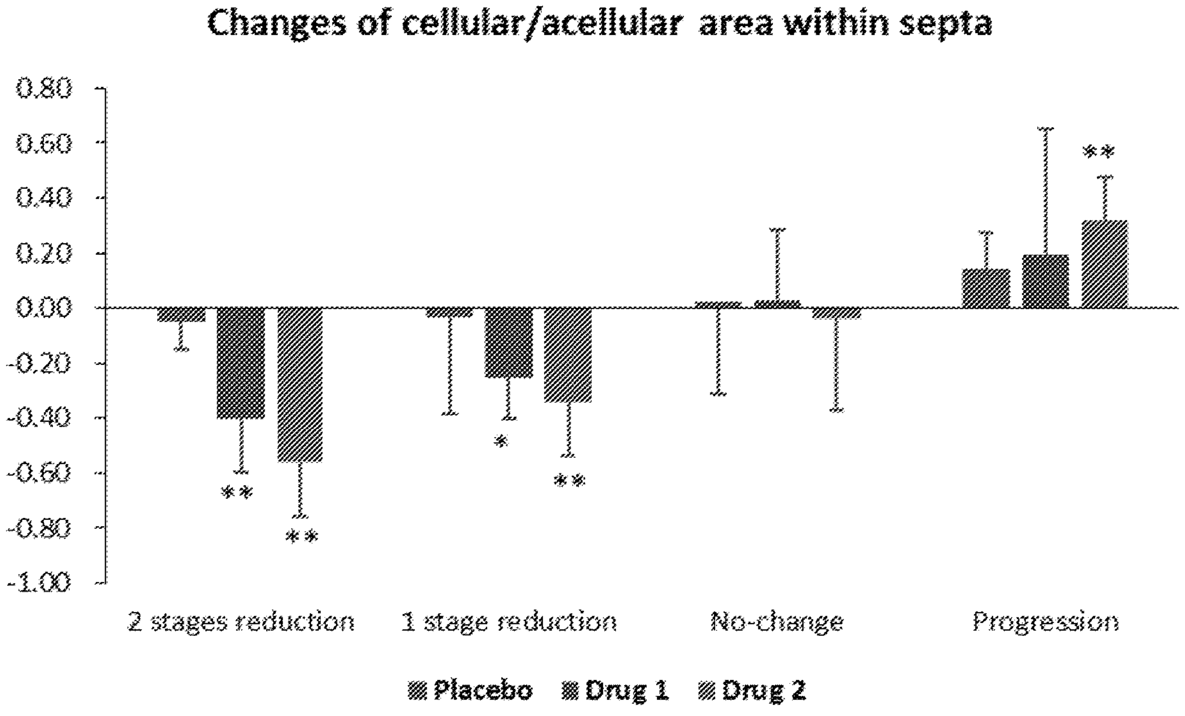
FIG. 9 shows changes in the cellular/acellular ratio and their correlation with regression or progression based on a comparison of different treatment regimes.

FIG. 9 shows an example of a correlation of the cellular/acellular ratio to fibrosis progression and regression, based on a comparison of placebo and two types of treatment. For example, a significant reduction of 0.4 or more provided by a treatment may correspond to 2-stage reduction, while a less significant reduction of about 0.3 or less provided by another treatment may correspond to a 1-stage reduction (based on NASH-CRN staging system). On the other hand, an increase may be indicative of progression.

Figure 10:
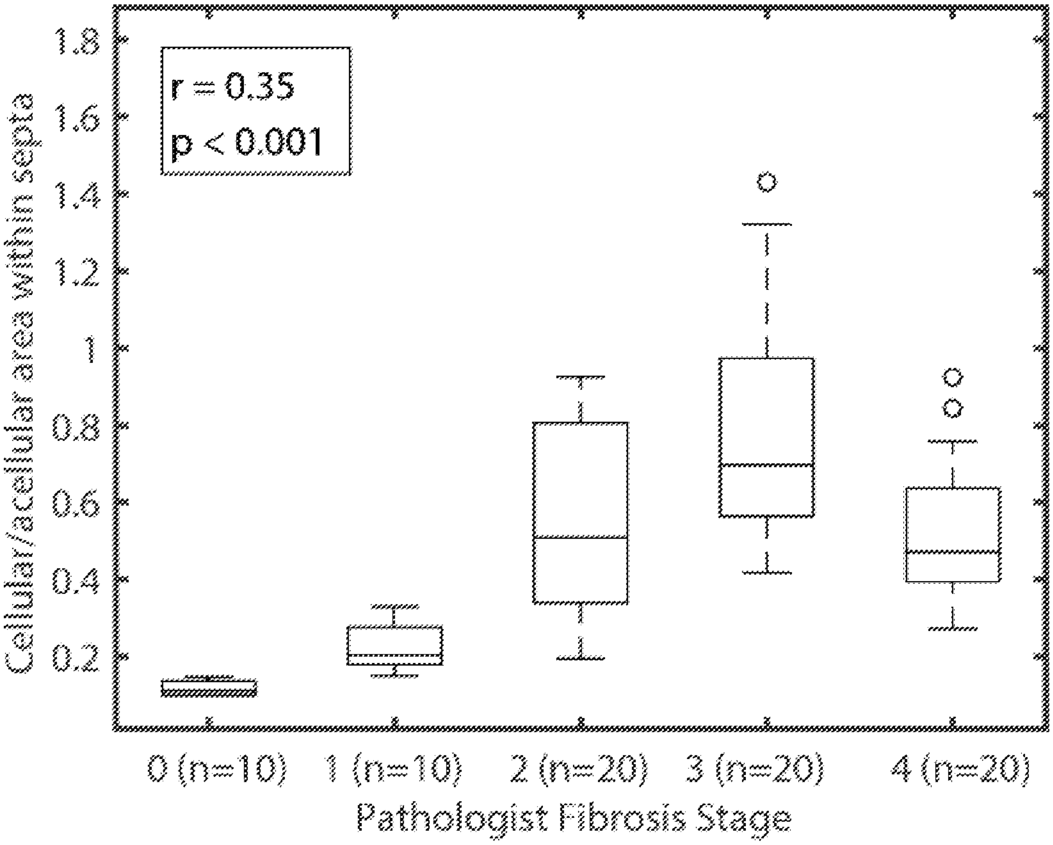
FIG. 10 shows an example boxplot illustrating a correlation between the cellular/acellular ratio and fibrosis stage.

FIG. 10 provides an alternative representation of the correlation between the cellular/acellular ratio and fibrosis state. In FIG. 10, ranges of absolute values of the cellular/acellular ratio based on various sample sizes are plotted against fibrosis stages as graded by a pathologist. It can be seen that there is a general upward trend from Stage 0 to Stage 3 before a drop at Stage 4. Thus, the parameter of cellular/acellular ratio can help to determine whether there has been a regression or progression.

In one example application, three patients with pathologically diagnosed NASH cirrhosis were studied. All three patients achieved a weight loss of more than 10% through lifestyle changes, and the second liver biopsy indicated that liver fibrosis decreased by one stage. The second harmonic generation/two-photon excitation fluorescence (SHG/TPEF) image technology was used to quantitively identify the changes in the septa and perisinusoidal area.

It was observed that the characteristics of the fibroseptal stroma in the first liver biopsy of the three cases showed mostly (more than 50%) wide/broad, loosely aggregated collagen which was consistent with the definition of "Predominantly progressive" of "Beijing classification". The specimens after weight loss showed the majority of thin and densely compacted stroma, which met the "Predominately regressive". A total of 20 progression septa, 27 reversal septa and 17 perisinusoidal fibrosis areas were labeled in the three paired specimens. The value of septa area (134406 vs. 13869 $\mu m^2$), septa length (896 vs. 445 μm), mean septa width (88 vs. 19 μm), max septa width (189 vs. 44 μm), and the cellular area within septa/septa area (0.240 vs. 0.120) of the "Progressive septa" were significantly higher than the "Regressive septa" (all $p<0.001$). In addition, the "Regressive septa" and perisinusoidal fibrosis were morphologically distinct. The "Regressive septa" had higher value of collagen area within septa/septa area (0.305 vs. 0.044, $p<0.001$), fiber within septa/septa area (0.012 vs. 0.002, $p<0.001$), aggregate collagen within septa/septa area (0.264 vs. 0.026, $p<0.001$), distribute collagen within septa/septa area (0.034 vs. 0.017, $p=0.008$), and lower value of cellular area within septa/septa area (0.123 vs. 0.772, $p<0.001$).

As disclosed, incorporating septa and nodules detection into ML algorithms can accurately detect septa and nodules in NASH cirrhotic patients. The method and system according to example embodiments can also correlate with HVPG and study the natural history of NASH cirrhosis and treatment response.

Figure 11:
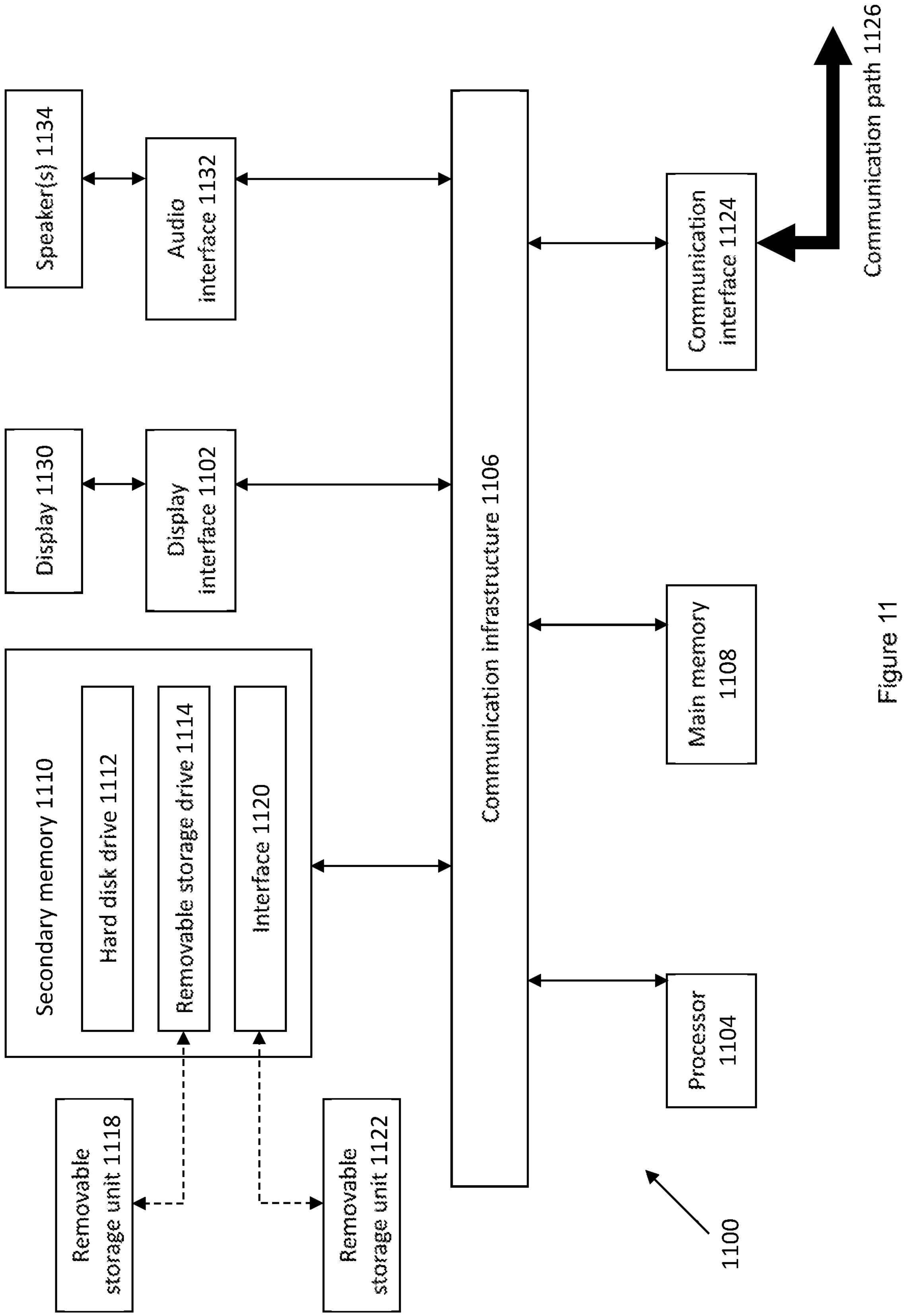
FIG. 11 shows a schematic diagram of a computer device capable of implementing aspects of the present method and system.

FIG. 11 depicts an exemplary computing device 1100, hereinafter Interchangeably referred to as a computer system 1100, where one or more such computing devices 1100 may be used for at least some steps of the present method. The following description of the computing device 1100 is provided by way of example only and is not intended to be limiting.

As shown in FIG. 11, the example computing device 1100 includes a processor 1104 for executing software routines. Although a single processor is shown for the sake of clarity, the computing device 1100 may also include a multiprocessor system. The processor 1104 is connected to a communication infrastructure 1106 for communication with other components of the computing device 1100. The communication infrastructure 1106 may include, for example, a communications bus, cross-bar, or network.

The computing device 1100 further includes a main memory 1108, such as a random access memory (RAM), and a secondary memory 1110. The secondary memory 1110 may include, for example, a hard disk drive 1112 and/or a removable storage drive 1114, which may include a floppy disk drive, a magnetic tape drive, an optical disk drive, or the like. The removable storage drive 1114 reads from and/or writes to a removable storage unit 1118 in a well-known manner. The removable storage unit 1118 may include a floppy disk, magnetic tape, optical disk, or the like, which is read by and written to by removable storage drive 1114. As will be appreciated by persons skilled in the relevant art(s), the removable storage unit 1118 includes a computer readable storage medium having stored therein computer executable program code instructions and/or data.

In an alternative implementation, the secondary memory 1110 may additionally or alternatively include other similar means for allowing computer programs or other instructions to be loaded into the computing device 1100. Such means can include, for example, a removable storage unit 1122 and an interface 1120. Examples of a removable storage unit 1122 and interface 1120 include a program cartridge and cartridge interface (such as that found in video game console devices), a removable memory chip (such as an EPROM or PROM) and associated socket, and other removable storage units 1122 and interfaces 1120 which allow software and data to be transferred from the removable storage unit 1122 to the computer system 1100.

The computing device 1100 also includes at least one communication interface 1124. The communication interface 1124 allows software and data to be transferred between computing device 1100 and external devices via a communication path 1126. In various embodiments of the inventions, the communication interface 1124 permits data to be transferred between the computing device 1100 and a data communication network, such as a public data or private data communication network. The communication interface 1124 may be used to exchange data between different computing devices 1100 which such computing devices 1100 form part an interconnected computer network. Examples of a communication interface 1124 can include a modem, a network interface (such as an Ethernet card), a communication port, an antenna with associated circuitry and the like. The communication interface 1124 may be wired or may be wireless. Software and data transferred via the communication interface 1124 are in the form of signals which can be electronic, electromagnetic, optical or other signals capable of being received by communication interface 1124. These signals are provided to the communication interface via the communication path 1126.

As shown in FIG. 11, the computing device 1100 further includes a display interface 802 which performs operations for rendering images to an associated display 1130 and an audio interface 1132 for performing operations for playing audio content via associated speaker(s) 1134.

As used herein, the term "computer program product" may refer, in part, to removable storage unit 1118, removable storage unit 1122, a hard disk installed in hard disk drive 1112, or a carrier wave carrying software over communication path 1126 (wireless link or cable) to communication interface 1124. Computer readable storage media refers to any non-transitory tangible storage medium that provides recorded instructions and/or data to the computing device 1100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computing device 1100. Examples of transitory or non-tangible computer readable transmission media that may also participate in the provision of software, application programs, instructions and/or data to the computing device 1100 include radio or infra-red transmission channels as well as a network connection to another computer or networked device, and the Internet or Intranets including e-mail transmissions and information recorded on Websites and the like.

The computer programs (also called computer program code) are stored in main memory 1108 and/or secondary memory 1110. Computer programs can also be received via the communication interface 1124. Such computer programs, when executed, enable the computing device 1100 to perform one or more features of embodiments discussed herein. In various embodiments, the computer programs, when executed, enable the processor 1104 to perform features of the above-described embodiments. Accordingly, such computer programs represent controllers of the computer system 1100.

Software may be stored in a computer program product and loaded into the computing device 1100 using the removable storage drive 1114, the hard disk drive 1112, or the interface 1120. Alternatively, the computer program product may be downloaded to the computer system 1100 over the communications path 1126. The software, when executed by the processor 1104, causes the computing device 1100 to perform functions of embodiments described herein.

It is to be understood that the embodiment of FIG. 11 is presented merely by way of example. Therefore, in some embodiments one or more features of the computing device 1100 may be omitted. Also, in some embodiments, one or more features of the computing device 1100 may be combined together. Additionally, in some embodiments, one or more features of the computing device 1100 may be split into one or more component parts.

It will be appreciated that the elements illustrated in FIG. 11 function to provide means for performing the various functions and operations of the servers as described in the above embodiments.

In an implementation, a server may be generally described as a physical device comprising at least one processor and at least one memory including computer program code. The at least one memory and the computer program code are configured to, with the at least one processor, cause the physical device to perform the requisite operations.

It will be appreciated by a person skilled in the art that numerous variations and/or modifications may be made to the present invention as shown in the specific embodiments without departing from the scope of the invention as broadly described. The present embodiments are, therefore, to be considered in all respects to be illustrative and not restrictive.

The invention claimed is:

1. A method for assessing nonalcoholic steatohepatitis (NASH) cirrhosis in a liver biopsy sample, the method comprising:

extracting, from the liver biopsy sample, image data indicative of one or more histopathological features, wherein the one or more histopathological features comprise septa and/or nodules and/or fibrosis; and analysing the extracted image data, using a machine learning model trained to assess the one or more histopathological features, to determine a degree of NASH cirrhosis, wherein training the machine learning model comprises:

providing a plurality of training samples and a plurality of validation samples, each sample comprising a graded liver biopsy sample;

quantifying parameters of the one or more histopathological features from image data of each of the training samples;

selecting a subset of quantified parameters of the one or more histopathological features;

constructing a model for assessing the one or more histopathological features from the subset of quantified parameters; and validating the constructed model using the validation samples, and wherein the one or more histopathological features comprise septa, and wherein quantifying parameters of septa further comprises determining a ratio of any two of a group consisting of a cellular area within septa, a collagen area within septa and a vessel area within septa.

2. The method as claimed in claim 1, wherein the image data is extracted by second harmonic generation (SHG) microscopy and/or two-photon excitation fluorescence (TPEF) microscopy.

3. The method as claimed in claim 1, wherein selecting the subset of quantified parameters comprises a sequential feature selection.

4. The method as claimed in claim 1, wherein validating the constructed model comprises a leave-one-out validation.

5. The method as claimed in claim 1, wherein the one or more histopathological features comprises a combination of all of septa, nodules and fibrosis.

6. The method as claimed in claim 1, wherein constructing the model comprises determining whether the model correlates with hepatic venous pressure gradient (HVPG) measurements.

7. The method as claimed in claim 6, wherein constructing the model comprises determining whether the model distinguishes a presence of varices.

8. The method as claimed in claim 6, wherein constructing the model comprises determining whether the model identifies hepatic venous pressure gradient (HVPG) changes outside a predetermined range.

9. A method for evaluating efficacy of a therapeutic intervention, the method comprising:

determining, from a first liver biopsy sample of a subject before the therapeutic intervention, a first degree of NASH cirrhosis using the method as claimed in claim 1;

determining, from a second liver biopsy sample of the subject after the therapeutic intervention, a second degree of NASH cirrhosis using the method as claimed in any one of the preceding claims; and comparing the first degree and second degree to determine efficacy of the therapeutic intervention.

10. A system for assessing nonalcoholic steatohepatitis (NASH) cirrhosis in a liver biopsy sample, the system comprising:

a processor; and a computer-readable memory coupled to the processor and having instructions stored thereon that are executable by the processor to:

receive image data of the liver biopsy sample indicative of one or more histopathological features, wherein the one or more histopathological features comprise septa and/or nodules and/or fibrosis; and analyse the image data, using a machine learning model trained to assess the one or more histopathological features, to determine a degree of NASH cirrhosis, wherein the machine learning model comprises:

quantified parameters of the one or more histopathological features, wherein the quantified parameters comprise a subset selected from parameters quantified from image data of each of a plurality of training samples, each training sample comprising a graded liver biopsy sample; and a model constructed from the subset of quantified parameters for assessing the one or more histopathological features, wherein the constructed model is validated using a plurality of validation samples, each validation sample comprises a graded liver biopsy sample, and wherein the one or more histopathological features comprise septa, and wherein the quantified parameters of the septa comprise a ratio of any two of a group consisting of a cellular area within septa, a collagen area within septa and a vessel area within septa.

11. The system as claimed in claim 10, wherein the image data comprises data from a second harmonic generation (SHG) microscope and/or a two-photon excitation fluorescence (TPEF) microscope.

12. The system as claimed in claim 10, wherein the subset of quantified parameters is selected by a sequential feature selection.

13. The system as claimed in claim 10, wherein the model constructed from the subset of quantified parameters is validated by a leave-one-out validation.

14. The system as claimed in claim 10, wherein the one or more histopathological features comprises a combination of all of septa, nodules and fibrosis.

15. The system as claimed in claim 10, wherein the model constructed from the subset of quantified parameters correlates with hepatic venous pressure gradient (HVPG) measurements.

16. The system as claimed in claim 15, wherein the model constructed from the subset of quantified parameters distinguishes a presence of varices.

17. The system as claimed in claim 15, wherein the model constructed from the subset of quantified parameters identifies hepatic venous pressure gradient (HVPG) changes outside a predetermined range.

* * * * *